United States Patent
Shuster et al.

(10) Patent No.: US 7,361,689 B2
(45) Date of Patent: Apr. 22, 2008

(54) ANTIBACTERIAL 1-(4-MONO- AND DI-HALOMETHYLSULPHONYLPHENYL)-2-ACYLAMINO-3-FLUOROPROPONALS AND PREPARATION THEREOF

(75) Inventors: Dale E. Shuster, South Orange, NJ (US); Scott Hecker, Del Mar, CA (US); Tomasz W. Glinka, Cupertino, CA (US); Rajeshwar Singh, Edmonton (CA); Zhuoyi Su, Edmonton (CA)

(73) Assignee: Schering-Plough Animal Health Corporation, Summit, NJ (US)

( * ) Notice: Subject to any disclaimer, the term of this patent is extended or adjusted under 35 U.S.C. 154(b) by 591 days.

(21) Appl. No.: 11/018,156

(22) Filed: Dec. 21, 2004

(65) Prior Publication Data

US 2005/0182139 A1 Aug. 18, 2005

Related U.S. Application Data

(60) Provisional application No. 60/533,724, filed on Dec. 31, 2003.

(51) Int. Cl.
*A61K 31/16* (2006.01)
*C07C 317/34* (2006.01)

(52) U.S. Cl. ..................... 514/628; 564/209
(58) Field of Classification Search ............... 514/628; 564/209
See application file for complete search history.

(56) References Cited

U.S. PATENT DOCUMENTS

| 2,776,992 | A | | 1/1957 | Gregory |
| 4,235,892 | A | | 11/1980 | Nagabhushan |
| 5,352,832 | A | | 10/1994 | Wu et al. |
| 7,041,670 | B2 | * | 5/2006 | Boojamra et al. .......... 514/242 |
| 2004/0082553 | A1 | | 4/2004 | Boojamra et al. |
| 2005/0182031 | A1 | | 8/2005 | Hecker et al. |

FOREIGN PATENT DOCUMENTS

EP 0 014 437 A2 8/1980

| WO | WO 03/077828 A2 | 9/2003 |
| WO | WO 2005/009429 A1 | 2/2005 |

OTHER PUBLICATIONS

Bolton, Lance F., et al., "Detection of Multidrug-Resistant . . . ," Journal of Clinical Microbiology 37(5):1348-1351 (May 1999).
Cloeckaert, Axel, et al. "Nonenzymatic Chloramphenicol Resistance . . . ," Antimicrobial Agent and Chemotherapy 45(8):2381-2382 (Aug. 2001).
Keyes, Kathleen, et al., "Detection of Florfenicol . . . ," Antimicrobial Agents and Chemotherapy 44(2):421-424 (Feb. 2000).
Kim, Eun-Heul, et al., "Sequence Analysis of the . . . ," Microbiol. Immunol. 40(9):665-669 (1996).
PCT International Search Report dated Jun. 27, 2005 for corresponding PCT Application No. PCT/US2004/043199.

* cited by examiner

*Primary Examiner*—Kamal A. Saeed

(57) ABSTRACT

Novel florfenicol compounds having the chemical structure:

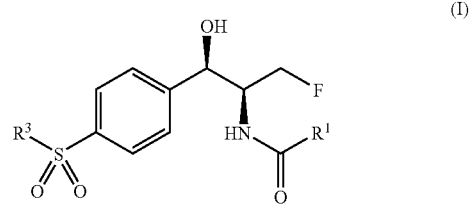

(I)

or a pharmaceutically-acceptable salt thereof or a solvate thereof, or prodrug thereof, wherein $R^1$ is $CHCl_2$, CHClF, $CHF_2$, CHBrCl, $CH_3$, $CH_2N_3$, $CH_2CN$, $CH(R_2)NH_2$ or CH $X^1X^2$; where $R^2$ is H, $CH_3$ or $CH_2OH$, and $X^1$ and $X^2$ are independently selected halogens; and $R^3$ is $CH_2Cl$, $CH_2F$, $CHF_2$, $CHCl_2$ or $CH_2OH$ are disclosed. The compounds are useful for the treatment and/or prevention of bacterial infections in a broad range of patients such as, without limitation, birds, fish, shellfish and mammals.

13 Claims, No Drawings

ANTIBACTERIAL 1-(4-MONO- AND DI-HALOMETHYLSULPHONYLPHENYL)-2-ACYLAMINO-3-FLUOROPROPONALS AND PREPARATION THEREOF

CROSS-REFERENCE TO RELATED APPLICATIONS

This application is a non-provisional application that claims priority under 35 U.S.C. § 119(e) of provisional application U.S. Ser. No. 60/533,724 filed Dec. 31, 2003, the contents of which are hereby incorporated by reference in their entireties.

FIELD OF THE INVENTION

The present invention relates to florfenicol analogs that are useful as antibiotics.

BACKGROUND OF THE INVENTION

Florfenicol is a broad spectrum antibiotic with activity against many gram-negative and gram-positive bacteria [see, e.g., U.S. Pat. Nos. 4,235,892, 5,352,832, the contents of which are hereby incorporated by reference in their entireties]. Specific analogs of florfenicol, recently have been reported [U.S. 20040082553, WO03/077828, the contents of which are hereby incorporated by reference in their entireties].

Florfenicol is useful for the prevention and treatment of bacterial infections due to susceptible pathogens in birds, reptiles, fish, shellfish and mammals. One of its primary uses is in the treatment of pneumonia and associated respiratory infections in cattle (often referred to generically as Bovine Respiratory Disease or BRD) caused by *Mannhemia haemolytica, Pasturella multocida* and(or) *Histophilus somni* (formerly *Haemophilus somnus*). It is also indicated in the treatment of pododermatitis in cattle caused by *Fusobacterium necrophorum* and/or *Bacterioides melaninogenicus*, swine respiratory disease caused by *Pasteurella multocida, Actinobacillus pleuropneumoniae, Streptococcus suis, Salmonella cholerasuis, Haemophilus parasuis*, and (or) *Mycoplasma* spp., colibacillosis in chickens caused by *Escherichia coli*, enteric septicemia in catfish caused by *Edwardsiella ictaluri*, and furunculosis in salmon caused by *Aeromonas salmonicida*. Other genera of bacteria that have exhibited susceptibility to florfenicol include *Enterobacter, Klebsiella, Staphylococcus, Enterococcus, Bordetella, Proteus*, and *Shigella*. In particular, chloramphenicol resistant strains of organisms such as *K. pneumoniae, E. cloacae, S. typhus* and *E. coli* are susceptible to florfenicol.

As shown below, florfenicol is a structural analog of both thiamphenicol and chloramphenicol.

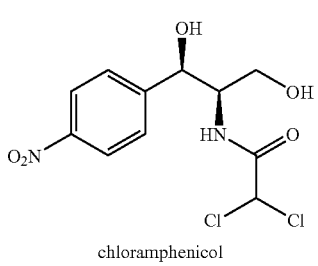

chloramphenicol

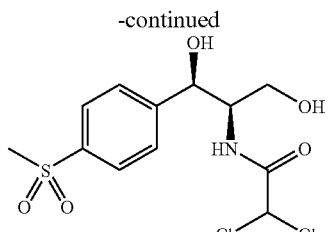

thiamphenicol

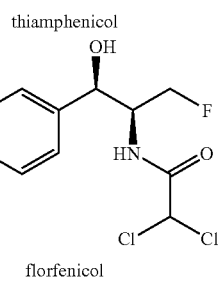

florfenicol

As is apparent, thiamphenicol differs from chloramphenicol by having an aromatic methylsulfonyl group in place of the aromatic nitro group. The aromatic nitro group of chloramphenicol has been implicated in chloramphenicol-induced, non-dose related irreversible aplastic anemia in humans, making thiamphenicol a safer choice in humans. Derivatives of thiamphenicol also have been reported [see, U.S. Pat. No. 2,776,992].

Like thiamphenicol, florfenicol differs from chloramphenicol by having an aromatic methylsulfonyl group in place of an aromatic nitro group. In addition, florfenicol also has a fluorine atom in place of the primary hydroxyl group found in both thiamphenicol and chloramphenicol.

Chloramphenicol, thiamphenicol, and florfenicol are potent antibiotics that inhibit bacterial protein synthesis through their binding to prokaryotic ribosomes. This binding interferes with the enzyme peptidyl transferase and its ability to catalyze protein chain elongation in the bacterium. A bacterial enzyme, chloramphenicol acetyl transferase (CAT), acetylates the primary hydroxyl group of chloramphenicol and thiamphenicol, greatly reducing their binding affinity for the bacterial ribosome, resulting in the deactivation of these antibiotics. The presence of a fluorine atom in place of the primary hydroxyl group makes florfenicol significantly less susceptible to deactivation by bacteria that encode CAT.

Unfortunately, a number of bacterial genera and species have begun to exhibit some resistance to florfenicol. For example, resistance has been observed in *Salmonella* species (Bolton, L. F., et al., *Clin. Microbiol.* 1999, 37, 1348), *E. coli* (Keyes, K., et al., *Antimicrob. Agents Chemother.*, 2000, 44, 421.), *Klebsiella pneumoniae* (Cloeckaert, A., et al., *Antimicrob. Agents Chemother.*, 2001, 45, 2381), and in the aquacultural pathogen, *Photobacterium damselae* subsp. *piscicida* (formerly *Pasteurella piscicida*) (Kim, E., et al., *Microbiol. Immunol.*, 1996, 40, 665). This resistance has been traced to a highly conserved gene, the florfenicol resistance gene (flo) that produces an antibiotic efflux pump (Flo).

The emergence, and threatened spread, of resistance to florfenicol has fostered the need for new antibiotics that retain or exceed the activity of florfenicol, maintain their imperviousness to the CAT enzyme, and, in addition, retain inhibitory activity against bacteria that have Flo efflux pump mediated antibiotic resistance.

The citation of any reference herein should not be construed as an admission that such reference is available as "Prior Art" to the instant application.

SUMMARY OF THE INVENTION

The present invention provides a solution to the problem caused by increasing bacterial resistance to chloramphenicol, thiamphenicol, and florfenicol by providing novel compounds with unexpectedly potent bacterial inhibitory properties. In one aspect, the present invention provides compounds that uniquely exhibit antimicrobial activity against bacterial strains that both (i) encode chloramphenicol acetyl transferase (CAT), and (ii) possess Flo efflux pump mediated antibiotic resistance. In a particular embodiment of this type, such compounds act as poor substrates of the FLO efflux pump.

One embodiment of this invention is a compound having the chemical formula:

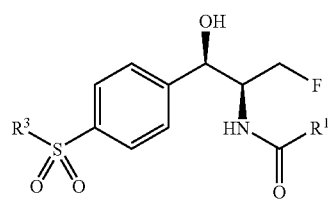

(I)

or a pharmaceutically-acceptable salt thereof or a solvate thereof, wherein:

$R^1$ is $CHCl_2$, $CHClF$, $CHF_2$, $CHBrCl$, $CH_3$, $CH_2N_3$, $CH_2CN$, $CH(R^2)NH_2$ or $CH\ X^1X^2$;

where: $R^2$ is H, $CH_3$ or $CH_2OH$, and $X^1$ and $X^2$ are independently selected halogens; and $R^3$ is $CH_2Cl$, $CH_2F$, $CHF_2$, $CHCl_2$ or $CH_2OH$.

In a preferred aspect of this embodiment, the compound is:

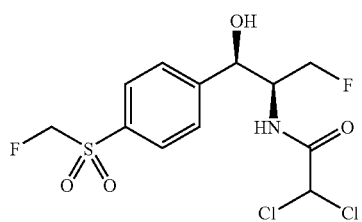

or a pharmaceutically-acceptable salt thereof or a solvate thereof and/or a prodrug thereof.

In a related aspect, the present invention provides prodrugs of the compounds of the present invention. In a particular embodiment of this type, the prodrug is a phosphate ester of the compound. In one such embodiment, the phosphate ester of the compound has the chemical structure:

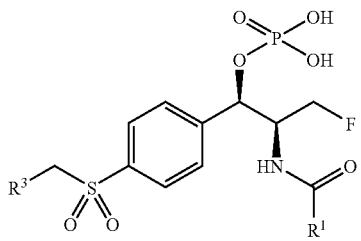

or a pharmaceutically-acceptable salt thereof, wherein: $R^1$ is $CHCl_2$, $CHClF$, $CHF_2$, $CHBrCl$, $CH_3$, $CH_2N_3$, $CH_2CN$, $CH(R^2)NH_2$ or $CH\ X^1X^2$;

$X^1$ and $X^2$ are independently selected halogens;

$R^2$ is H, $CH_3$ or $CH_2OH$, and $R^3$ is $CH_2Cl$, $CH_2F$, $CHF_2$, $CHCl_2$ or $CH_2OH$.

In a particular embodiment of this type, the compound comprises the chemical structure:

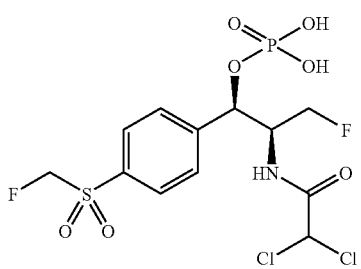

The present invention further provides methods of treating or preventing bacterial infections by administering the compounds of the present invention, pharmaceutically-acceptable salts thereof, solvates thereof and/or prodrugs thereof. The present invention further provides methods of preparing the compounds of the present invention, as well as the pharmaceutically-acceptable salts thereof, solvates thereof and/or prodrugs thereof.

In a particular embodiment of the present invention, a pharmaceutical composition is administered parenterally. Parenteral administration may involve intramuscular or intravenous injection. Parenteral administration may also involve subcutaneous injection. In another embodiment, a pharmaceutical composition of the present invention is administered orally. In a particular embodiment of this type, a pharmaceutical composition of the present invention is in an aqueous solution. In one such embodiment, the pharmaceutical composition is placed into a liquid to be ingested by the subject, e.g., into its drinking water.

DETAILED DESCRIPTION OF THE INVENTION

Therefore, the present invention provides novel compounds that can act as antibiotics. Preferably, these compounds possess favorable antibacterial profiles that heretofore, were unattainable by known phenicol-type antibiotics.

In one embodiment of the invention there are provided compounds corresponding to Formula (I):

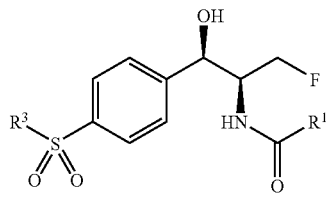
(I)

or a pharmaceutically-acceptable salt thereof or a solvate thereof, wherein:

$R^1$ is $CHCl_2$, $CHClF$, $CHF_2$, $CHBrCl$, $CH_3$, $CH_2N_3$, $CH_2CN$, $CH(R^2)NH_2$ or $CH\,X^1X^2$; where $R^2$ is H, $CH_3$ or $CH_2OH$, $X^1$ and $X^2$ are independently-selected halogens; and $R^3$ is $CH_2Cl$, $CH_2F$, $CHF_2$, $CHCl_2$ or $CH_2OH$.

Some preferred aspects of this embodiment include those in which $R^1$ is $CHCl_2$ and $R^3$ is $CH_2F$.

In other aspects of the invention, $X^1$ and $X^2$ are independently selected halogens which may be the same or different halogens. Preferably, the halogen is fluorine, chlorine or bromine. One preferred embodiment is where both $X^1$ and $X^2$ are chlorine. The 1-(4-mono- and di-halomethylsulphonylphenyl)-2-acylamino-3-fluoropropanols of the present invention can be synthesized inter alia, by the methods provided in the Examples and Schemes provided below.

Table 1 shows structures of representative compounds of this invention. The table and the compounds therein are not intended, nor should they be construed, to limit this invention in any manner whatsoever.

TABLE 1

| Compound No. | STRUCTURE |
| --- | --- |
| 1 | |
| 2 | |
| 3 | 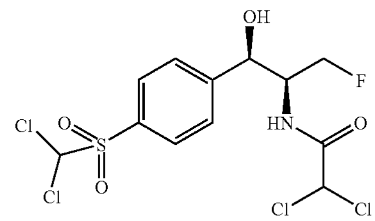 |
| 4 | 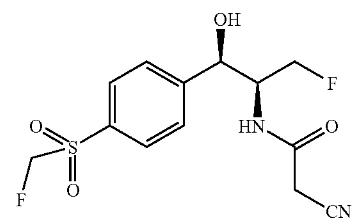 |
| 5 | 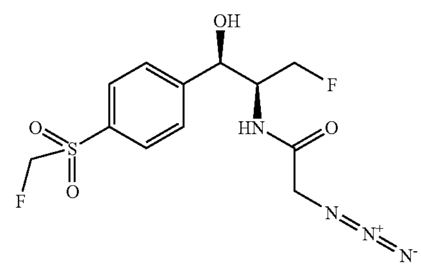 |
| 6 | 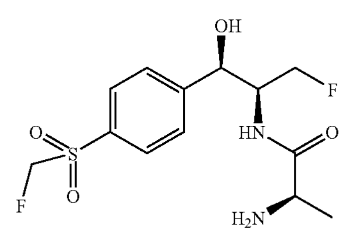 |
| 7 | 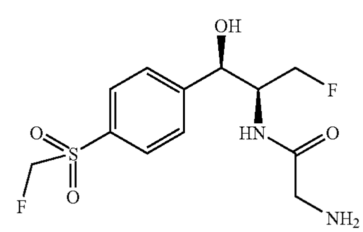 |
| 8 | 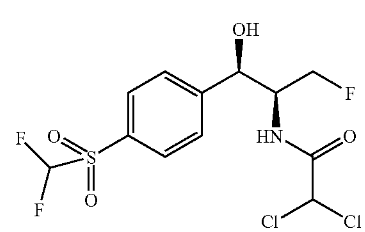 |

TABLE 1-continued

| Compound No. | STRUCTURE |
|---|---|
| 9 | *(structure)* |
| 10 | *(structure)* |
| 11 | *(structure)* |
| 12 | *(structure)* |

In a preferred aspect of this embodiment, the compound is:

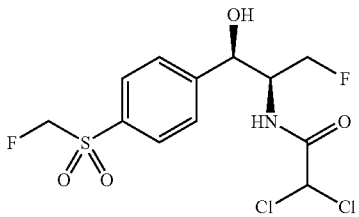

or a pharmaceutically-acceptable salt thereof or a solvate thereof.

In order to more fully appreciate the instant invention, the following definitions are provided.

As used herein, "halo" and "halogen" refers to fluorine, chlorine, bromine or iodine.

As used herein, "relative stereochemistry" refers to the positioning in space of substituents relative to one another.

As used herein, "absolute stereochemistry" refers to the exact positioning of substituents in three-dimensional space as determined by the Cahn-Ingold-Prelog rules, the application of which are well-known to those skilled in the art.

As used herein, an "enantiomer" refers to one of the two absolute stereochemical configurations of a molecule that rotates plane polarized light in one direction or the other (i.e., counterclockwise from its original axis, conventionally called "left," or clockwise, conventionally referred to as "right"). By "substantially enantiomerically pure" is meant that the compound consists of greater than 90% of the one enantiomer, preferably greater than 95%, and most preferably greater than 99%.

As used herein, a "racemate" refers to a 1:1 mixture of the two enantiomers of a compound. Racemic mixtures are designated by a (+/−) indicator. Substantially enantiomerically pure compounds are shown without the indicator.

As used herein, the term "patient" is used interchangeably with the term "subject" and the term "animal subject" and refers to an animal species capable of being infected by a pathogenic bacterium, and in a particular embodiment includes humans. Appropriate animal patients also include those in the wild, livestock (e.g., raised for meat, milk, butter, eggs, fur, leather, feathers and/or wool), beasts of burden, research animals, companion animals, as well as those raised for/in zoos, wild habitats and/or circuses. In a particular embodiment a "subject" of the invention is a "food producing" animal. For purposes of the present invention, the term "food-producing" animal shall be understood to include all animals bred for consumption, or for consumables (e.g., dairy cows, egg-laying hens and the like) by humans and/or other animals. A non-limiting list of such animals include avians (chickens, turkeys, geese, duck, ostriches, etc.), bovines (e.g., cattle, dairy cows, buffalo), ovines (e.g., goats or sheep), porcines (e.g., hogs or pigs), equines (e.g., horses) etc., as well as aquatic animals including shellfish and fish such as trout or salmon, and other species raised or harvested for human consumption.

In another embodiment, the patient is a companion animal. For purposes of the present invention, the term "companion" animal shall be understood to include housecats (feline), dogs (canine), rabbit species, horses (equine), rodents (e.g., guinea pigs, squirrels, rats, mice, gerbils, and hamsters), primates (e.g., monkeys) and avians, such as pigeons, doves, parrots, parakeets, macaws, canaries, and the like.

Other animals are also contemplated to benefit from the inventive compounds of the present invention, including marsupials (such as kangaroos), reptiles (such as farmed turtles), game birds, swans, ratites and other economically important domestic animals.

Other mammalian subjects include bovid animals and swine. The term "bovid" refers to animals in the family Bovidae, which includes hoofed, hollow-horned ruminants such as cattle, sheep, goats, buffaloes, oxen, etc. As used herein, the term "swine" refers to animals of the family Suidae, which includes pigs, boars, warthogs, etc.

As used herein, the term "composition" is intended to encompass a product comprising the specified ingredients in the specified amounts, as well as any product which results, directly or indirectly, from combination of the specified ingredients in the specified amounts.

An "effective amount" or a "pharmaceutically-effective amount" is the dose required to alleviate a particular symptom of an infection or disease or to protect a patient or an animal against infections or disease.

The compounds of the invention, and the compounds employed in the methods of the present invention can also form stable complexes with solvent molecules that remain intact after the non-complexed solvent molecules are removed from the compounds. These complexes are referred to herein as "solvates". Solvates of the compounds of the present invention are also included in the present invention. In a particular embodiment, the solvent molecule is water.

The compounds, salts thereof, solvates thereof and pharmaceutical compositions of the presnet invention are useful for the treatment of bacterial infections in patients. As such, one embodiment of this invention is a method of treating or preventing a bacterial infection which comprises administering to a patient in need thereof a pharmaceutically-effective amount of a compound of formula (I) hereof.

In an embodiment of this invention, the bacterial infection is caused by bacteria of one or more of the genera *Pasteurella, Histophilus, Haemophilus, Fusobacterium, Bacterioides, Aeromonas, Enterobacter, Escherichia, Klebsiella, Salmonella, Shigella, Actinobacillus, Streptococcus, Mycoplasma, Edwardsiella, Staphylococcus, Enterococcus, Bordetella, Proteus,* and *Mannheimia*.

In another embodiment of this invention, the bacterial infection is caused by one or more of *Mannhemia haemolytica, Pasteurella multocida, Histophilus somni, Haemophilus parasuis, Fusobacterium necrophorum, Bacterioides melaninogenicus, Actinobacillus pleuropneumoniae, Streptococcus suis, Salmonella cholerasuis, Mycoplasma bovis, Mycoplasma hyopneumoniae, Mycoplasma hyorhinis, Mycoplasma gallisepticum, Edwardsiella ictaluri, Escherichia coli, Enterobacter cloacae, Staphylococcus aureus, Staphylococcus intermedius, Enterococcus faecalis, Enterococcus faecium, Klebsiella pneumoniae, Klebsiella oxytoca, Enterobacter cloacae, Proteus mirabilis,* and *Aeromonas salmonicida*.

Phosphate Esters

A phosphate ester of a 1-(4-mono- and di-halomethylsulphonylphenyl)-2-acylamino-3-fluoropropanol of the present invention can be synthesized by any of a number of methods. The synthesis of a particular 1-(4-mono-halomethylsulphonylphenyl)-2-acylamino-3-fluoropropanol, as shown below,

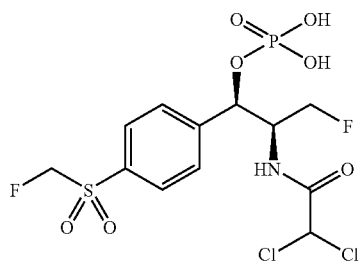

is provided simply to exemplify the general methodology [see also U.S. provisional application No. 60/532,227, filed Dec. 23, 2003 and corresponding U.S. non-provisional application PCT/US04/43199, filed, Dec. 21, 2004, which it claims priority therefrom, the contents of both applications are hereby incorporated by reference in their entireties.]

Thus, a chosen 1-(4-mono- and di-halomethylsulphonylphenyl)-2-acylamino-3-fluoropropanol can be synthesized by one of the methods provided in the Examples and Schemes provided below. In this exemplification, the phosphate ester and/or salt thereof of the particular compound shown above may be prepared from the corresponding 1-(4-fluoromethylsulphonylphenyl)-2-acylamino-3-fluoropropanol as follows. Reacting the 1-(4-fluoromethylsulphonylphenyl)-2-acylamino-3-fluoropropanol with di-tert-butylphosphoramidite in the presence of tetrazole, in a first suitable solvent (e.g., tetrahydrofuran), to yield a first intermediate. Next, an oxidant (e.g., m-chloroperbenzoic acid) can be added in a second suitable solvent (e.g., dichloromethane) to the first intermediate, to yield a second intermediate. After isolating the second intermediate (e.g., by flash column chromatography), the second intermediate can be dissolved in a third suitable solvent (e.g., dichloromethane). The second intermediate then can be reacted with trifluoroacetic acid to yield a 1-(4-fluoromethylsulphonylphenyl)-2-acylamino-3-fluoropropanol phosphate ester in its acid form. The acid form of 1-(4-fluoromethylsulphonylphenyl)-2-acylamino-3-fluoropropanol phosphate ester can subsequently be isolated.

The first intermediate produced in the reaction with di-tert-butylphosphoramidite described above, can be converted into the second intermediate, without the need of it being isolated or purified, when an appropriate oxidant is employed (e.g., m-chloroperbenzoic acid). Similarly, the second intermediate can be converted into the acidic form of a deprotected phosphate ester by treatment with an acid (e.g., trifluoroacitic acid) without the need of isolating or purifying the second intermediate.

The isolated acid form of the 1-(4-fluoromethylsulphonylphenyl)-2-acylamino-3-fluoropropanol phosphate ester then can be added to (or combined with) a solution of a base that comprises a pharmaceutically-acceptable cation. In one such embodiment, the base is an inorganic base, such as sodium hydroxide, potassium hydroxide, sodium carbonate, potassium carbonate, sodium bicarbonate, ammonium hydroxide, or one that comprises a pharmaceutically-acceptable cation (e.g., calcium hydroxide). In an alternative embodiment, the base is an organic base that comprises a pharmaceutically-acceptable cation (e.g., a protonated amine) or di-cation (e.g., bis-protonated diamine). A salt form of the phosphate ester of the 1-(4-fluoromethylsulphonylphenyl)-2-acylamino-3-fluoropropanol can then be isolated, yielding an isolated phosphate ester of the 1-(4-fluoromethylsulphonylphenyl)-2-acylamino-3-fluoropropanol with a pharmaceutically-acceptable cation or dication.

Pharmaceutical Compositions

A compound of the present invention, a prodrug thereof or a physiologically acceptable salt of either the compound or its prodrug, may be administered as such to a patient or may be administered in pharmaceutical compositions in which the foregoing materials are mixed with suitable excipient(s). Techniques for formulation and administration of drugs may be found in *Remington's Pharmacological Sciences*, Mack Publishing Co., Easton, Pa., latest edition. The formulations and techniques discussed in Remington relate primarily to use with human patients; however, they readily may be modified for use with non-human patients by techniques well-known to those skilled in the veterinary art.

Routes of Administration

As used herein, "administer" or "administration" refers to the delivery of a compound, salt or prodrug of the present invention or of a pharmaceutical composition containing a compound, salt or prodrug of this invention to an organism for the purpose of treating or preventing a microbial infection.

Suitable routes of administration may include, without limitation, oral, rectal, topical, transmucosal, intramuscular, subcutaneous, intramedullary, intrathecal, direct intraventricular, intravenous, intravitreal, intraperitoneal, intranasal, aural or intraocular. The preferred routes of administration are oral and parenteral.

Alternatively, one may administer the compound in a local rather than systemic manner, for example, by preparation as a salve or topically applied formulation that is applied directly to the infected area or by injection of the compound directly into infected tissue. In either case, a sustained release formulation may be used.

Thus, administration of the compounds of the invention, or their pharmaceutically acceptable salts, in pure form or in an appropriate pharmaceutical composition, can be carried out via any of the accepted modes of administration or agents for serving similar utilities. The routes of administration can be any known to those of ordinary skill. The inventive compounds are given to those in need thereof in any art recognized form, i.e., solid, semi-solid, lyophilized powder, or liquid dosage forms, such as for example, tablets, suppositories, pills, soft elastic and hard gelatin capsules, powders, solutions, suspensions, or aerosols, or the like, in unit or multi-dosage forms suitable for simple administration of precise dosages. The compositions will include a conventional pharmaceutical carrier or excipient and a compound of the invention as the active agent, and, in addition, may include other medicinal agents, pharmaceutical agents, carriers, adjuvants, etc.

Composition/Formulation

Pharmaceutical compositions of the present invention may be manufactured by processes well known in the art, e.g., using a variety of well-known mixing, dissolving, granulating, dragee-making, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen.

For injection, including, without limitation, intravenous, intramusclular and subcutaneous injection, the compounds of the invention may be formulated in aqueous solutions, preferably in physiologically compatible buffers such as Hanks' solution, Ringer's solution, physiological saline buffer or polar solvents including, without limitation, propylene glycol, ethanol, polyethylene glycol, and N-methyl-2-pyrrolidone, 2-pyrrolidone, other pyrrolidones, N,N-dimethylacetamide, N,N-dimethylformamide, dimethylsulfoxide, acetone, triacetin, glycerol formal, as well as combinations of any of the foregoing excipients or other materials known to those of ordinary skill. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl- methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers also may be added in these formulations.

For administration by inhalation, the compounds of the present invention can conveniently be delivered in the form of an aerosol spray using a pressurized pack or a nebulizer and a suitable propellant, e.g., without limitation, dichlorodifluoro-methane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular or subcutaneous injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, although often at the risk of greater toxicity.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed.

Pharmaceutical compositions useful herein also may comprise solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Dosage

A therapeutically effective amount refers to an amount of compound effective to prevent, alleviate or ameliorate symptoms of a microbial infection. Determination of a therapeutically effective amount is well within the capability of those skilled in the art, especially in light of the disclosure herein.

For any compound used in the methods of the invention, the therapeutically effective amount can be estimated initially from cell culture assays. Then, the dosage can be formulated for use in animal models so as to achieve a circulating concentration range that includes the MIC as determined in cell culture. Such information can then be used to more accurately determine dosages useful in patients.

Toxicity and therapeutic efficacy of the compounds described herein can be determined by standard pharmaceutical procedures in cell cultures or experimental animals. For example, the MIC and the $LD_{50}$ for a particular compound can be determined by methods well-known in the art. The data obtained can be used to formulate a range of dosages useful in patients. The dosage, of course, may vary depending upon the dosage form and route of administration. The exact formulation, route of administration and dosage can be selected by the individual physician in view of the patient's condition. (See e.g., Fingl, et al., 1975, in "*The Pharmacological Basis of Therapeutics*", Ch. 1 p. 1). In general, however, the presently preferred dosage range for systemic delivery of a compound of this invention will be from about 1 to about 100 mg/kg/day and is preferably from about 2 to about 60 mg/kg/day.

Dosage amount and interval may be adjusted individually to provide plasma levels of the compound that are sufficient to maintain a concentration equal to the MIC or any other desired level. Such plasma levels are often referred to as minimum effective concentrations (MECs). The MEC will vary for each compound but can be estimated from in vitro data, e.g., the concentration necessary to achieve 80+% inhibition of a microbe, may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time.

In cases of local administration or selective uptake, the effective local concentration of the drug may not be related to plasma concentration and other procedures known in the art may be employed to determine the correct dosage amount and interval.

The compositions may be administered once daily or divided into multiple doses. Often only one dose will be sufficient to treat the infection. In some circumstances one dose followed by a second dose 48 hours later will be required to treat the animal. The precise dose will depend on the stage and severity of the infection, the susceptibility of the infecting organism to the composition, and the individual characteristics of the animal species being treated, as will be appreciated by one of ordinary skill in the art.

The amount of a composition administered will, of course, be dependent on the patient being treated, pathogen or bacteria causing the infection, the severity of the infection, the manner of administration i.e., oral, intravenous, topical, etc., the judgment of the prescribing physician, veterinarian, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition.

Aquatic Uses

An embodiment of the invention includes methods of eliminating, reducing or preventing bacterial infections in fish. The methods include administering an effective amount of a compound of Formula I to a fish in need thereof. In most aspects of this embodiment, treatment is effected by either feeding the fish an effective amount of the inventive compound or by immersing the fish or fish population in a solution which contains an effective amount of the active compound in solution. It is to be further understood that the inventive compound can be administered by application of the drug to a pool or other water-holding area containing the fish and allowing the fish to absorb the active through their gills or otherwise allowing the dosage of the inventive compound to be taken in by the fish.

Any fish species, including fresh water and salt water varieties, can be treated with the compounds of the present invention to eliminate or reduce bacteria.

For purposes of the present invention, the term "fish" shall be understood to include without limitation, for example, those fish in the Teleosti grouping of fish, i.e., teleosts. Both the Salmoniformes order (which includes the Salmonidae family) and the Perciformes order (which includes the Centrarchidae family) are contained within the Teleosti grouping.

Examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed *Plecostomus* (*Plecostomus* spp).

*Salmonidae* Family

| | |
|---|---|
| *Coregonus clupeaformis* | Lake whitefish |
| *Coregonus hoyi* | Bloater |
| *Oncorhynchus keta* | Chum salmon |
| *Oncorhynchus gorbuscha* | Pink salmon |
| *Oncorhynchus kisutch* | Coho salmon (silver salmon) |
| *Oncorhynchus masou* | Cherry salmon (*masou* salmon) |
| *Oncorhynchus nerka* | Sockeye salmon |
| *Oncorhynchus tshawytscha* | King salmon (*chinook* salmon) |
| *Prosopium cylindraceum* | Round whitefish |
| *Oncorhynchus clarki* | Cutthroat trout |
| *Oncorhynchus mykiss* | Rainbow trout |
| *Salmo salar* | Atlantic salmon |
| *Salmo trutta* | Brown trout |
| *Salmo trutta* X *S. fontinalis* | Tiger hybrid-trout |
| *Salvelinus alpinus* | Arctic charr |
| *Salvelinus confluentus* | Bull trout |
| *Salvelinus fontinalis* | Brook trout |
| *Salvelinus leucomaenis* | Japanese charr (white spotted charr) |
| *Salvelinus malma* | Dolly varden (*Miyabe charr*) |
| *Salvelinus namaycush* | Lake trout |
| *Thymallus thymallus* | Grayling |

Some Members of the *Serranidae* Family

| TAXON NAME | COMMON NAME |
|---|---|
| *Centropristis ocyurus* | Bank sea bass |
| *Centropristis philadelphicus* | Rock sea bass |
| *Centropristis striata* | Black sea bass |
| *Diplectrum bivittatum* | Dwarf sandperch |
| *Diplectrum formosum* | Sand perch |
| *Epinephelus flavolimbatus* | Yellowedge grouper |
| *Epinephelus morio* | Red grouper |
| *Serranus phoebe* | Tattler |
| *Serranus tortugarum* | Chalk bass |

Some Members of the *Sparidae* family

| TAXON NAME | COMMON NAME |
|---|---|
| *Archosargus probatocephalus* | Sheepshead |
| *Archosargus rhomboidalis* | Sea bream |
| *Calamus penna* | Sheepshead porgy |
| *Lagodon rhomboides* | Pinfish |
| *Pagrus Major* | Red Sea bream |
| *Sparus aurata* | Gilthead Sea bream |
| *Stenotomus chrysops* | Scup |

Some Members of the *Cichlidae* family

| TAXON NAME | COMMON NAME |
|---|---|
| *Aequidens latifrons* | Blue acara |
| *Cichlisoma nigrofasciatum* | Congo cichlid |
| *Crenichichla* sp. | Pike cichild |
| *Pterophyllum scalare* | Angel fish |
| *Tilapia mossambica* | Mozambique mouth breeder |
| *Oreochromis* spp. | Tilapia |
| *Sarotherodon aurea* | Golden Tilapia |

Some Members of the *Centrarchidae* family

| TAXON NAME | COMMON NAME |
|---|---|
| *Ambloplites rupestris* | Rock bass |
| *Centrarchus macropterus* | Flier |
| *Elassoma evergladei* | Everglades pigmy sunfish |
| *Elassoma okefenokee* | Okefenokee pigmy sunfish |
| *Elassoma zonatum* | Banded pigmy sunfish |
| *Enneacanthus gloriosus* | Bluespotted sunfish |
| *Enneacanthus obesus* | Banded sunfish |
| *Lepomis auritus* | Redbreast sunfish |
| *Lepomis cyanellus* | Green sunfish |
| *Lepomis cyanellus* X *L. gibbosus* | Green x pumpkinseed |
| *Lepomis gibbosus* | Pumpkinseed |
| *Lepomis gulosus* | Warmouth |
| *Lepomis humilis* | Orange-spotted sunfish |
| *Lepomis macrochirus* | Bluegill |
| *Lepomis megalotis* | Longear sunfish |
| *Micropterus coosae* | Shoal bass |
| *Micropterus dolomieui* | Smailmouth bass |
| *Micropterus punctulatus* | Spotted bass |
| *Micropterus salmoides* | Largemouth bass |
| *Pomoxis annularis* | White crappie |
| *Pomoxis nigromaculatus* | Black crappie |

Still further examples of fish that can be treated include, but are not limited to catfish, sea bass, tuna, halibut, arctic charr, sturgeon, turbot, flounder, sole, carp, tilapia, striped bass, eel, sea bream, yellowtail, amberjack, grouper and milkfish.

The dose of the inventive compounds that is effective for reducing, eliminating, or preventing the bacterial infection can be routinely determined by a veterinarian, although it may vary depending on the species of fish treated, the particular parasites involved, and the degree of infestation. Preferably, the amount of the active compound or a salt thereof fed to fish will be at a dose of from about 1 to 100 mg per kg of fish biomass per day. More preferably, the amount will be from about 2 mg to about 60 mg per kg of fish biomass per day.

While the active ingredient can be administered separately from fish food, it is contemplated that in a preferred aspect that the active will be incorporated into the fish feed. A medicated fish feed may be prepared by incorporating a suitable amount of compound of the present invention or a salt thereof into a commercially available fish feed product to achieve the desired dosing levels. The amount of compound of the present invention incorporated into the fish feed will depend on the rate at which the fish are fed. For fish fed at the rate of about 0.2% to 4% of biomass/day, the medicated feed preferably contains from about 50 to 10,000 mg per kg of feed, and more preferably, from about 100 to 2,000 mg per kg of feed.

Although compound of the present invention can be incorporated into a feed mixture prior to pelleting, the medicated feed is preferably formed by coating feed pellets with compound of the present invention.

The present invention may be better understood by reference to the following non-limiting examples, which are provided as exemplary of the invention. The following examples are presented in order to more fully illustrate embodiments of the invention and should in no way be construed as limiting the broad scope of the invention.

EXAMPLES

The following examples are provided to illustrate certain embodiments of this invention and are not intended, nor are they to be construed, to limit its scope in any manner whatsoever.

Syntheses

For purposes of illustration and not limitation, Scheme 1 below is provided to illustrate the synthetic pathway for preparing Compound 1 in Table 1.

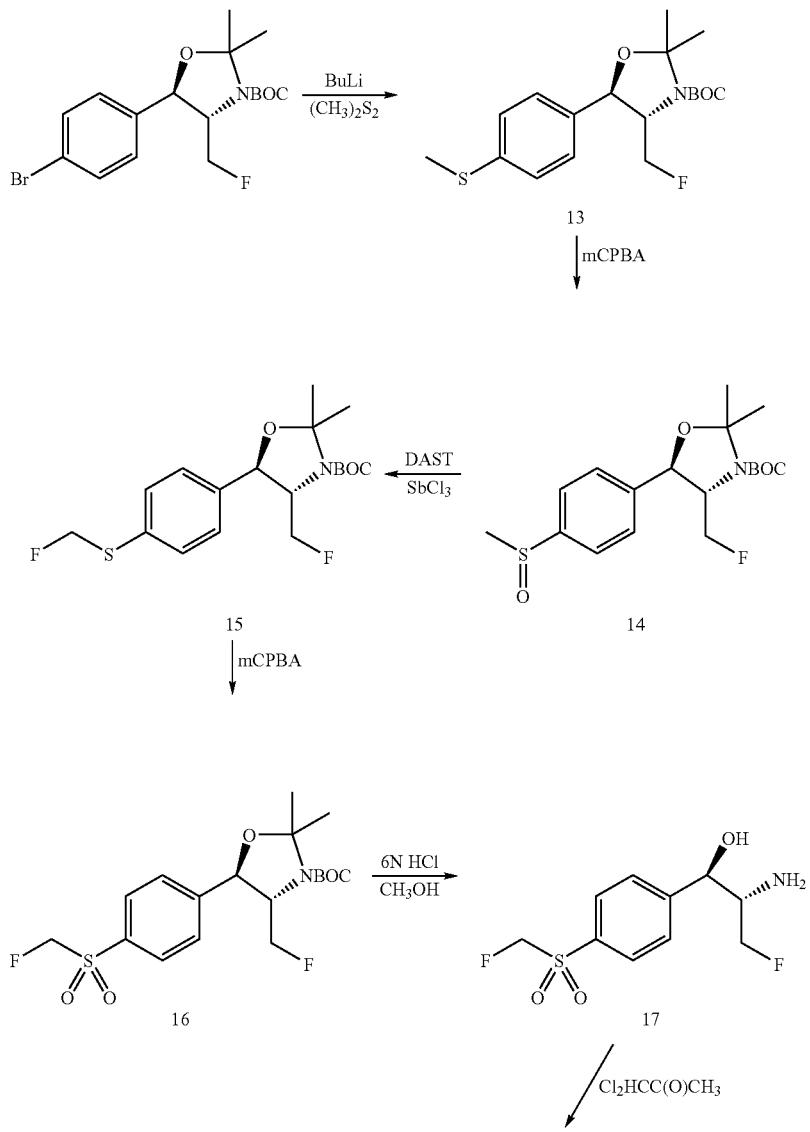

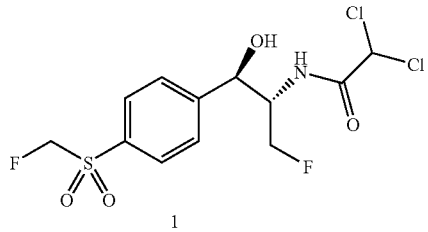

Example 1 tert-Butyl-(4S,5R)-4-(fluoromethyl)-2,2-dimethyl-5-(4-methylthiophenyl)-1,3-oxazolidine-3-carboxylate (13)

N-butyl lithium (n-BuLi), (1.78 g, 28 mmol, 1.2 eq) was added to a solution of tert-butyl (4S,5R)-5-(4-bromophenyl)-4-(fluoromethyl)-2,2-dimethyl-1,3-oxazolidine-3-carboxylate (9.0 g, 23 mmol) in 30 ml of anhydrous tetrahydrofuran (THF) at −78° C. in 30 min, and the reaction mixture was stirred for 30 minutes under $N_2$. 3.1 ml of dimethyldisulfide (1.5 eq) was added, and stirred for 30 min. The reaction mixture was warmed up to room temperature and stirred for 1 hour. A saturated solution of ammonium chloride (50 ml) and ethyl acetate (50 ml) was added and stirred for 30 min. The organic layer was washed with brine (50 ml) and dried over sodium sulfate. After purification, via a column, 8.15 g of white solid of the desired product was obtained.

$^1$H NMR (400 MHz, CDCl3): σ 1.49 (s, 9H), 1.54 (s, 3H), 1.72 (s, 3H), 2.48 (s, 3H), 3.79 (m, 1H), 4.40 (m, 1H), 5.06 (d, 2H, J=7.2 Hz), 7.26 (m, 2H), 7.40 (m, 2H).

Example 2 tert-Butyl(4S,5R)-4-(fluoromethyl)-2,2-dimethyl-5-[4-(methylsulfinyl)phenyl]-1,3-oxazolidine-3-carboxylate (14)

A solution of m-chloroperbenzoic acid (14.3 g, 1.2 eq) in 100 ml of dichloromethane was added drop wise to the solution of 13 (17.3 g) in 150 ml of dichloromethane at −20° C. The temperature was maintained at −20° C. for an additional 40 minutes. A saturated solution of sodium bicarbonate (80 ml) was added and stirred for 30 minutes. The organic layer was separated and washed with brine (50 ml) and dried over sodium sulfate. After purification (via a column) 13.4 g of the desired product (as a heavy oil) was obtained.

$^1$H NMR (400 MHz, CDCl3): σ 1.50 (s, 9H), 1.59 (s, 3H), 1.77 (s, 3H), 2.72 (s, 3H), 3.85 (m, 1H), 4.53 (m, 1H), 5.17 (d, 2H, J=8.8 Hz), 7.56 (m, 2H), 7.67 (m, 2H).

Example 3 tert-Butyl(4S,5R)-4-(fluoromethyl)-2,2-dimethyl-5-[4-(fluoromethylthio)phenyl]-1,3-oxazolidine-3-carboxylate (15)

A solution of diethylamino sulfurtrifluoride (DAST), (9.34 g, 1.75 eq) in 10 ml of dichloromethane was added drop wise to the solution of 14 (12.3 g) and antimony (III) chloride (0.23 g, 0.03 eq) in 150 ml of dichloromethane (anhydrous) at −5° C., and the reaction mixture was warmed up to room temperature overnight. A cold saturated solution of sodium bicarbonate (80 ml) was added and stirred for 30 min and extracted with dichloromethane (100 ml×2). The organic layer was washed with a 10% solution of sodium bicarbonate and with brine (50 ml) and dried over sodium sulfate. After purification, via a column, 10.7 g of the desired product (as a heavy oil) was obtained.

$^1$H NMR (400 MHz, CDCl3): σ 1.50 (s, 9H), 1.58 (s, 3H), 1.70 (s, 3H), 3.81 (m, 1H), 4.49 (m, 1H), 5.10 (d, 2H, J=7.2 Hz), 5.70 (d, 2H, J=52.8 Hz), 7.41 (m, 2H), 7.52 (m, 2H).

Example 4 tert-Butyl(4S,5R)-4-(fluoromethyl)-2,2-dimethyl-5-[4-(fluoromethylsulfonyl)phenyl]-1,3-oxazolidine-3-carboxylate (16)

A solution of m-chloroperbenzoic acid (14.8 g, 3 eq) in 50 ml of dichloromethane was added drop wise to a solution of 15 (10.7 g) in 100 ml of dichloromethane at −10° C. and the reaction mixture was warmed up to room temperature (overnight). A saturated solution of sodium bicarbonate (100 ml) was added and stirred for 30 min at 0° C. and extracted with dichloromethane (100 ml×3). The organic layer was washed with brine and dried over sodium sulfate and concentrated. After purification (via a column) 11.6 g of the desired product (as heavy oil) was obtained.

$^1$H NMR (400 MHz, CDCl3): σ 1.49 (s, 9H), 1.59 (s, 3H), 1.71 (s, 3H), 3.88 (m, 1H), 4.48 (m, 1H), 5.08 (d, 2H, J=47.2 Hz), 5.23 (d, 2H, J=7.2 Hz), 7.69 (m, 2H), 7.98 (m, 2H).

Example 5

(1R,2S)-2-Amino-3-fluoro-1-{4-[(fluoromethyl)sulfonyl]phenyl}propan-1-ol (17)

A solution of 6N HCl (30 ml, 5.5 eq) was added to a solution of 16 (12.0 g) in 200 ml of MeOH at room temperature, and the reaction mixture was warmed up to 40° C. overnight. Methanol was removed in vacuo. The reaction mixture was washed with diethyl ether (50 ml×2). The aqueous solution was neutralized with 2N NaOH and extracted with ethyl acetate (100 ml×3). The organic layer was washed with brine, dried over sodium sulfate, and concentrated to provide the pure desired product (7.6 g).

$^1$H NMR (400 MHz, CD3OD): σ 3.12 (m, 1H), 4.28 (m, 1H), 4.38 (m, 1H), 4.80 (m, 2H), 7.69 (m, 2H), 7.95 (m, 2H).

Example 6

N-((1S,2R)-1-(Fluoromethyl)-2-{4-[(fluoromethyl)sulfonyl]phenyl}-2-hydroxyethyl)-2,2-dichloroacetamide (1)

Methyl dichloroacetate (23.2 g, 5 eq ) and triethylamine (33.0 g, 10 eq) was added to a solution of 17 (8.64 g) in 50 ml of MeOH at room temperature. The reaction mixture was stirred overnight. Methanol was removed in vacuo. The residue was dissolved in 250 ml of ethyl acetate and washed with 1N HCl. The organic layer was washed with a 10% solution of sodium bicarbonate and brine and dried over sodium sulfate and concentrated to dryness. After purification via a column, 11.7 g of the desired product was obtained as a white solid.

$^1$H NMR (400 MHz, CDCl3): σ 2.85 (m, 1H), 4.50 (m, 1H), 4.72 (m, 1H), 5.06 (d, 2H, J=47.2 Hz), 5.27 (t, 2H, J=3.6 Hz), 5.82 (s, 1H), 6.97 (d, 1H, J=8.0), 7.63 (m, 2H), 7.93 (m, 2H).

SCHEME 2
ALTERNATIVE SYNTHETIC APPROACH TO COMPOUND 1 FROM THIOMICAMINE

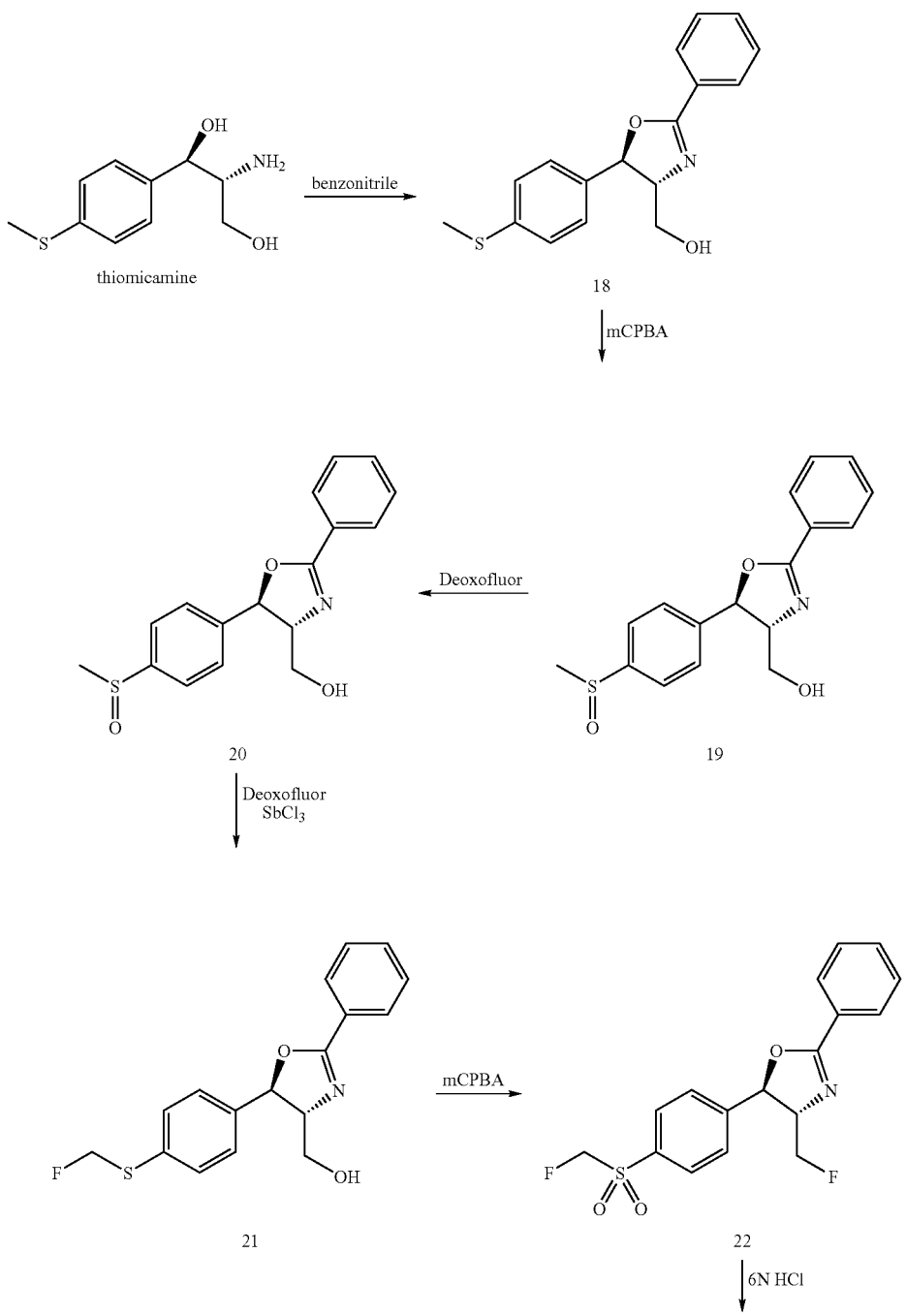

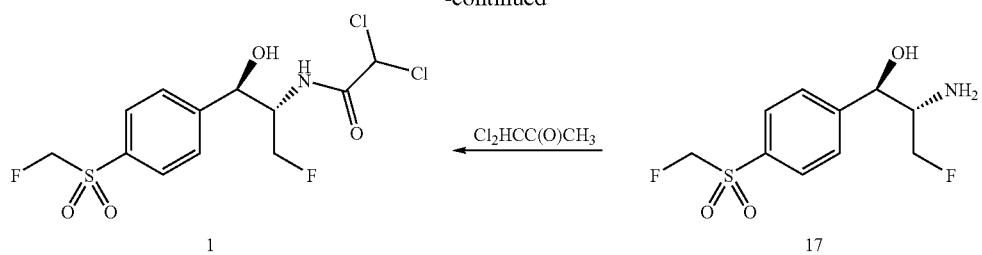

Example 7

{(4R,5R)-5-[4-(Methylthio)phenyl]-2-phenyl-4,5-dihydro-1,3-oxazol-4-yl}methanol (18)

A mixture of thiomicamine (10 g, 46.88 mmol) and K$_2$CO$_3$ (0.97 g, 7.03 mmol) in 16 mL of ethylene glycol and 10 mL of glycerol was heated to 100° C. to obtain a clear brown solution. Benzonitrile (9.6 mL, 93.76 mmol) was added and the resulting mixture was stirred at 105° C. for 14 hours. It was cooled to room temperature and diluted with water to afford a white suspension. Filtering, washing with water (500 mL) and hexanes (300 mL), and drying under vacuum provided 13.3 g of the desired product as a light yellow solid. $^1$H NMR (400 MHz, CD$_3$OD) 2.48 (s, 3H), 3.70-3.90 (m, 2H), 4.10-4.20 (m, 1H), 5.57 (d, J=7 Hz, 1H), 7.30 (s, 4H), 7.48 (t, J=8 Hz, 2H), 7.57 (t, J=8 Hz, 1H), 8.0 (d, J=8 Hz, 2H).

Example 8

{(4R,5R)-5-[4-(Methylsulfinyl)phenyl]-2-phenyl-4,5-dihydro-1,3-oxazol-4-yl}methanol (19)

To a solution of sulfide 18 (5 g, 16.7 mmol) in dichloromethane (200 mL) at −78° C. was added m-chloroperbenzoic acid (3.6 g, 16.7 mmol) in dichloromethane (150 mL) over a span of 10 minutes. The resulting mixture was stirred at −78° C. for 30 minutes. The reaction was quenched with aqueous NaHCO$_3$ at −78° C. Extraction with dichloromethane (3×200 mL) afforded 5.22 g of the desired sulfoxide as a white solid, upon concentration. $^1$H NMR (200 MHz, CDCl$_3$) 2.72 (s, 3H), 3.80-3.90 (m, 1H), 4.05-4.15 (m, 1H), 4.20-4.30 (m, 1H), 5.61 (d, J=8 Hz, 1H), 7.35-7.55 (m, 5H), 7.68 (t, J=9 Hz, 2H), 8.0 (d, J=9 Hz, 2H).

Example 9

(4S,5R)-4-(Fluoromethyl)-5-{4-[(fluoromethyl)thio]phenyl}-2-phenyl-4,5-dihydro-1,3-oxazole (21)

To a solution of sulfoxide 19 (0.5 g, 1.59 mmol) in dichloromethane (100 mL) at 0° C. was added bis-(2-methoxyethyl)aminosulfur trifluoride (Deoxofluor), (1.1 mL, 5.57 mmol). The resulting mixture was stirred at 0° C. for 1 hour and then at room temperature for 6 hours. Antimony trichloride (22 mg, 0.095 mmol) was added and the resulting mixture was stirred at room temperature for 14 hours and then at reflux for 3 hours. The reaction was quenched with aqueous NaHCO$_3$. Extraction with dichloromethane (2×50 mL) afforded an oil residue upon concentration which was subjected to flash chromatography (SiO$_2$, hexanes/ethyl acetate=5:1) to provide 0.45 g of the desired product as a colorless oil. $^1$H NMR (400 MHz, CDCl$_3$) 4.34-4.43 (m, 1H), 4.55-4.80 (m, 2H), 5.56 (d, J=8 Hz, 1H), 5.65 (s, 1H), 5.79 (s, 1H), 7.34 (d, J=9 Hz, 2H), 7.47 (t, J=9 Hz, 2H), 7.51-7.55 (m, 3H), 8.04 (d, J=9 Hz, 2H).

Example 10

(4S,5R)-4-(Fluoromethyl)-5-{4-[(fluoromethyl)sulfonyl]phenyl}-2-phenyl-4,5-dihydro-1,3-oxazole (22)

To a solution of sulfide 20 (0.5 g, 1.57 mmol) in dichloromethane (100 mL) at RT was added m-chloroperbenzoic acid (0.845 g, 3.92 mmol). The resulting mixture was stirred at RT for 14 hours. The reaction was quenched with aqueous NaHCO$_3$. Extraction with dichloromethane (2×100 mL) afforded 5.7 g of the desired sulfone as a white solid, upon concentration. $^1$H NMR (400 MHz, CDCl$_3$) 4.36-4.43 (m, 1H), 4.55-4.86 (m, 2H), 5.07 (s, 1H), 5.20 (s, 1H), 5.70 (d, J=7 Hz, 1H), 7.48 (t, J=9 Hz, 2H), 7.55-7.63 (m, 3H), 7.97-8.06 (m, 4H).

Example 11

(1R,2S)-2-Amino-3-fluoro-1-{4-[(fluoromethyl)sulfonyl]phenyl}propan-1-ol (17)

A solution of sulfone 22 (1.47 g, 4.19 mmol) in dichloromethane (50 mL) was mixed with 6N HCl (40 mL). Dichloromethane was distilled out and the resulting white suspension was stirred at reflux for 14 hours. It was cooled to room temperature and treated with aqueous NaHCO$_3$ to pH=8~9. Extraction with dichloromethane (3×50 mL) afforded an oil residue which was subjected to flash chromatography (SiO$_2$, hexanes/ethyl acetate=2:1 to ethyl acetate 100%) to provide 1.0 g of the desired product, as a light yellow oil. $^1$H NMR (400 MHz, CDCl$_3$) 3.05-3.15 (m, 1H), 4.24-4.52 (m, 2H), 4.72 (d, J=6 Hz, 1H), 5.09 (s, 1H), 5.21 (s, 1H), 7.62 (d, J=9 Hz, 2H), 7.93 (d, J=9 Hz, 2H).

Example 12

N-((1S,2R)-1-(Fluoromethyl)-2-{4-[(fluoromethyl)sulfonyl]phenyl}-2-hydroxyethyl)-2,2-dichloroacetamide (1)

A mixture of 17 (0.90 g, 3.39 mmol), methyl dichloroacetate (0.42 mL, 4.07 mmol) and triethylamine (0.71 mL, 5.09 mmol) in methanol (40 mL) was stirred at 40° C. for 20 hours. The reaction was quenched with water. Extraction with dichloromethane (2×100 mL) afforded an oily residue which was subjected to flash chromatography (SiO$_2$, hexanes/ethyl acetate=2:1 to 1:1) to provide 0.98 g of the desired product as a white solid. $^1$H NMR (400 MHz, CDCl$_3$) 4.28-4.38 (m, 1H), 4.46-4.72 (m, 2H), 5.05 (s, 1H), 5.17 (s, 1H), 5.23 (t, J=4 Hz, 1H), 5.81 (s, 1H), 7.01 (d, J=8 Hz, 1H), 7.62 (d, J=8 Hz, 2H), 7.87 (d, J=8 Hz, 2H).

drop-wise over 2 hours. The reaction mixture was stirred at −20 to −25° C. for 3 hours under nitrogen atmosphere. The reaction mixture was quenched with saturated NaHCO$_3$ (5.8 L) at −20° C. The organic layer was separated, washed with

SCHEME 3
ALTERNATIVE SYNTHETIC APPROACH TO INTERMEDIATE 21 FROM THIOMICAMINE

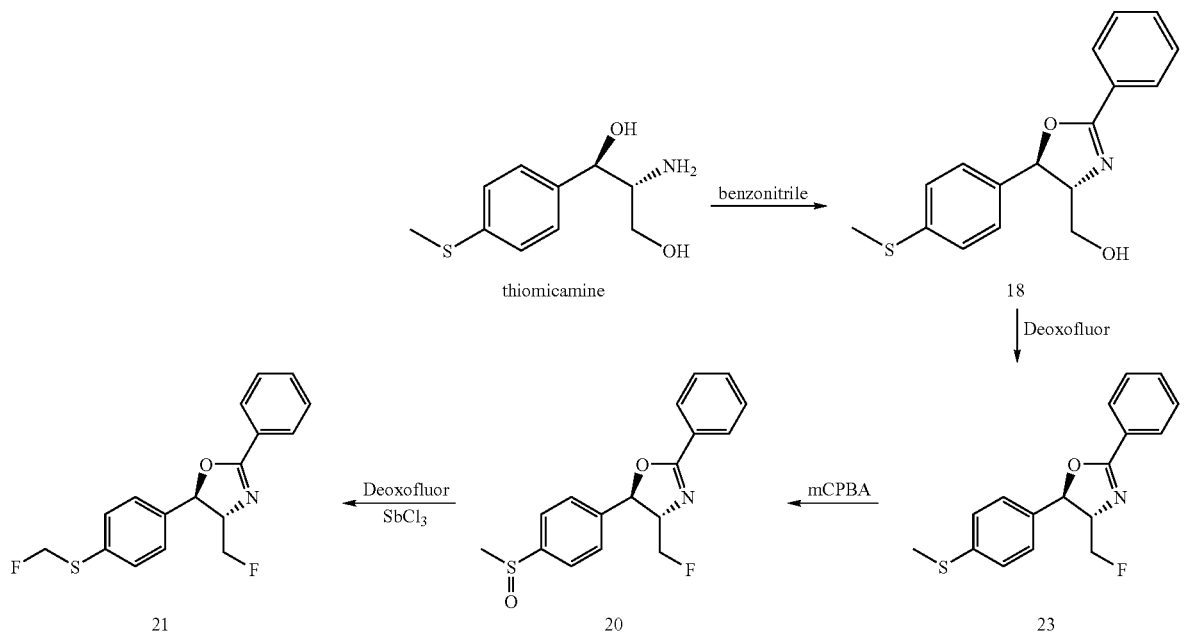

Example 13

(4S,5R)-4-(Fluoromethyl)-5-[4-(methylthio)phenyl]-2-phenyl-4,5-dihydro-1,3-oxazole (23)

To a suspension of 18 (1200 g, 4.0 mol) in anhydrous dichloromethane (12 L) at −78° C., Deoxofluor (1419 g, 1.18 mol) was added drop-wise. The reaction mixture was allowed to warm up to room temperature and stirred for 72 hours under a nitrogen atmosphere. The reaction mixture was cooled to 0° C. A saturated NaHCO$_3$ solution was added slowly to the reaction mixture until a pH=5-6 was obtained. The organic layer was separated. The aqueous layer was extracted with dichloromethane (2×4 L). The combined organic layers were washed with brine (2×4 L) and then concentrated to afford a yellow solid as a crude product which was subjected to column chromatography (SiO$_2$, ethyl acetate/hexane=1:3) to provide 613.1 g of the desired product. $^1$H NMR (400 MHz, CD$_3$OD) 2.42 (s, 3 H), 4.28-4.30 (m, 1H), 4.32-4.36 (m, 1H), 4.59-4.62 (m, 2H), 4.72-4.78 (m, 2H), 5.59 (d, J=8 Hz, 1 H), 7.24 (s, 4 H), 7.43-7.46 (m, 2H), 7.56-7.59 (m, 1H), 8.00-8.04 (m, 2H).

Example 14

(4S,5R)-4-(Fluoromethyl)-5-[4-(methylsulfinyl)phenyl]-2-phenyl-4,5-dihydro-1,3-oxazole (20)

To a solution of 23 (334.31 g, 1.11 mol) in anhydrous dichloromethane (5.46 L) at −30° C., mCPBA (255.29 g, 1.11 mol) in anhydrous dichloromethane (3.45 L) was added water (3×2 L), brine (2 L), dried over Na$_2$SO$_4$ and concentrated to provide 358 g of crude desired product. $^1$H NMR (400 MHz, CD$_3$OD) 2.80 (s, 3 H), 4.34-4.43 (m, 1H), 4.48-4.52 (m, 1H), 4.65-4.70 (m, 2H), 4.72-4.80 (m, 2H), 5.79 (d, J=8 Hz, 1 H), 7.45-7.48 (m, 2 H), 7.58-7.62 (m, 3H), 7.76-7.89 (m, 2H), 8.02-8.10 (m, 2H). The crude material was used directly in the next step.

Example 15

(4S,5R)-4-(Fluoromethyl)-5-{4-[(fluoromethyl)thio]phenyl}-2-phenyl-4,5-dihydro-1,3-oxazole (21)

To a solution of 20 (390.9 g, 1.11 mol) and SbCl$_3$ (7.62 g, 0.0334 mol) in anhydrous dichloromethane (2.27 L) at −15° C., diethylamino sulfurtrifluoride (DAST) (258 ml, 2.0 mol) was added drop-wise. The reaction mixture was stirred for 3 hours at −20° C. and then allowed to warm up to room temperature overnight. The reaction was quenched with 1N NaOH solution until pH=3-4 at −20° C., and then solid NaHCO$_3$ was added to pH=8. The organic layer was separated and the aqueous solution was extracted with dichloromethane. The combined organic extracts were washed with water, brine, dried over Na$_2$SO$_4$ and concentrated to provide 330 g of the desired product as a brown oil.

SCHEME 4
ANOTHER ALTERNATIVE SYNTHETIC APPROACH TO INTERMEDIATE 21 FROM THIOMICAMINE

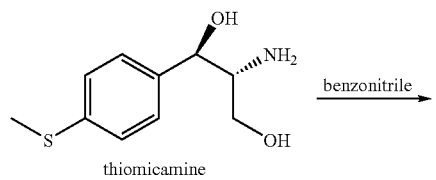

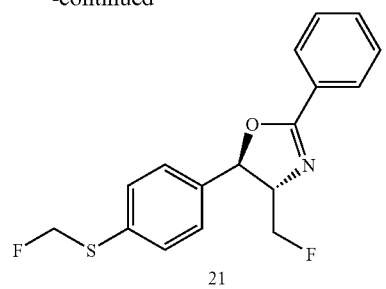

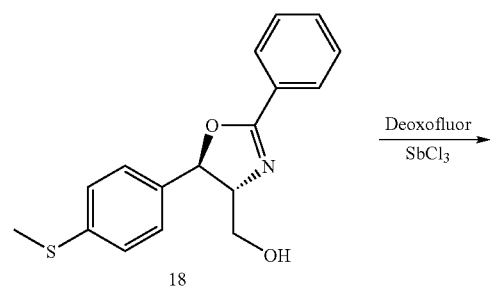

Example 16

(4S,5R)-4-(Fluoromethyl)-5-{4-[(fluoromethyl)thio]phenyl}-2-phenyl-4,5-dihydro-1,3-oxazole (21)

To a suspension of 18 (1200 g, 4.0 mol) in anhydrous dichloromethane (10 L) at −30° C., Deoxofluor (1500 g, 6.4 mol) was added drop-wise. The reaction mixture was allowed to warm up to room temperature and stirred for 48 hours under a nitrogen atmosphere. The reaction mixture was cooled to −30° C. To the reaction mixture SbCl$_3$ (72.0 g, 0.315 mol) was added and then Deoxofluor (1300 g, 5.2 mol) was added drop-wise. The reaction mixture was allowed to warm up to room temperature and stirred for 66 hours under a nitrogen atmosphere. The reaction mixture was cooled to −30° C., and then a saturated NaHCO$_3$ solution (14 L) was added slowly until pH=7. The organic layer was separated and washed with brine (4 L) and dried over Na$_2$SO$_4$, then concentrated to afford a crude product which was subjected to column chromatography (SiO$_2$, ethyl acetate/hexane=1:4, 1:2.5) to provide 995.9 g of the desired product.

SCHEME 5
PREPARATION OF DICHLOROMETHYLSULFONYL, COMPOUND 3

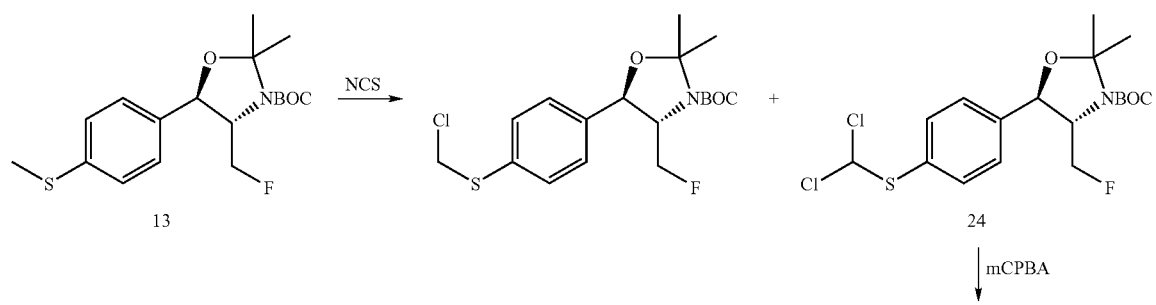

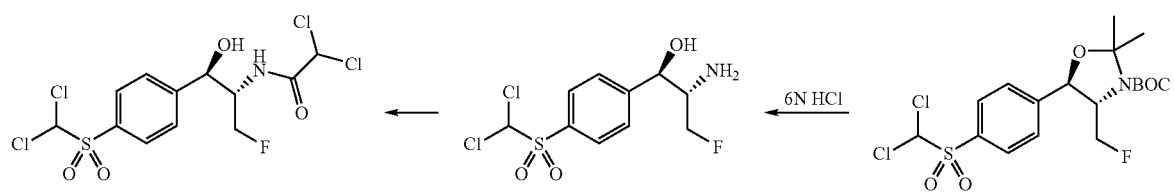

SCHEME 6
PREPARATION OF THE DIFLUORMETHYLSULFONYL, COMPOUND 8

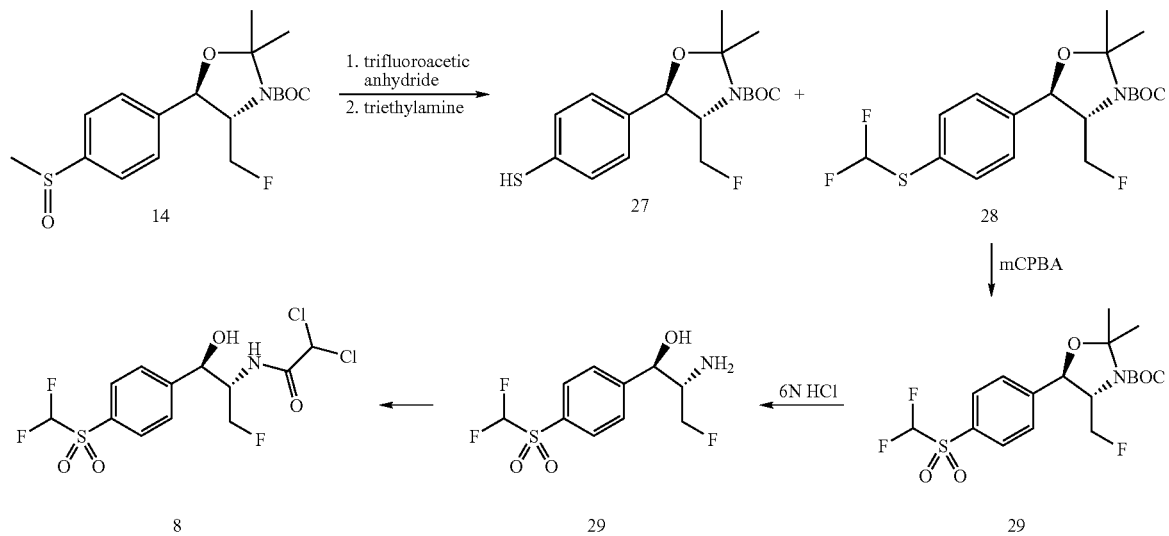

Example 17

Biological Evaluation

All of the compounds of this invention are expected to demonstrate antimicrobial activity against the same bacteria as the other members of the chloramphenicol family. In addition, they may be expected to be active against species of bacteria that are resistant to current chloramphenicol antibiotics, in particular florfenicol. It is also expected that the present compounds may exhibit activity against genera and species of bacteria against which current chloramphenicol-type antibiotics are not active.

It is also understood that, with regard to bioactivity, one enantiomer of a compound may be more active than the other. In such case, whether expressly stated or not, the more active isomer is considered the preferred embodiment of this invention, when all remaining factors are equal (e.g., toxicity effects, solubility etc.) One particular embodiment is an enantiomer of any given compound of the present invention having the 1-(R)-2(S) absolute configuration.

To determine the range and level of activity of the compounds of this invention, the following protocols may be used. Other such protocols will become apparent to those skilled in the art based on the disclosures herein and are within the scope of this invention. Some compounds herein are expected to not only exhibit substantial antibacterial activity but to also be less susceptible to current chloramphenicol resistance mechanisms. The screening protocols herein may be used to determine such characteristics also.

Susceptibility Testing

Table 2 is a list of the microorganisms against which the compounds of this invention were tested. The list is not intended, nor should it be construed, to limit the scope of this invention in any manner whatsoever.

TABLE 2

MINIMAL INHIBITORY CONCENTRATION AGAINST BACTERIAL STRAINS.
[microgram/milliliter (μg/ml) of compound]

| Compound | Escherichia coli | Pasteurella multocida | Florfenicol-resistant Pasteurella multocida | Mannheimia haemolytica | Staphylococcus aureus |
| --- | --- | --- | --- | --- | --- |
| Thiamphenicol | 64 | 0.25 | Not tested | 1 | Not tested |
| Chloramphenicol | 4 | 0.25 | 16 | 1 | 8 |
| Florfenicol | 8 | 0.25 | 16 | 1 | 8 |
| 1 | 4 | 0.06 | 2 | 0.5 | 2 |
| 2 | 32 | 1 | 8 | 0.5 | 16 |
| 3 | >128 | 0.5 | 4 | 0.5 | 8 |
| 4 | 16 | 1 | >128 | 0.5 | 8 |
| 5 | 8 | 0.25 | 16 | 0.25 | 8 |
| 6 | 32 | 1 | 128 | 1 | 64 |
| 7 | 128 | 1 | >128 | 1 | 64 |
| 8 | 16 | 0.125 | 2 | 0.5 | 4 |
| 9 | 4 | 0.25 | 8 | 0.5 | 8 |
| 10 | 8 | 0.25 | 4 | 0.5 | 4 |

TABLE 2-continued

MINIMAL INHIBITORY CONCENTRATION AGAINST BACTERIAL STRAINS.
[microgram/milliliter (μg/ml) of compound]

| Compound | Escherichia coli | Pasteurella multocida | Florfenicol-resistant Pasteurella multocida | Mannheimia haemolytica | Staphylococcus aureus |
|---|---|---|---|---|---|
| 11 | 4 | 0.25 | 4 | 0.25 | 2 |
| 12 | >128 | 1 | 32 | 2 | >128 |

Compounds were tested for antimicrobial activity against several bacterial stains using standard broth microdilution susceptibility testing methodology (NCCLS, 2002), The results demonstrate that all compounds have comparable or better activity than florfenicol against one or more of the strains tested. The enhanced activity of Compound 1 is especially noteworthy. It is more active than florfenicol for all five bacterial strains, and this compound is 8-fold more activity against florfenicol-resistant *Pasteurella multocida*.

Reference

NCCLS. 2002. Performance standards for antimicrobial disk and dilution susceptibility tests for bacteria isolated from animals; approved standard-second edition. NCCLS document M31-A2 [ISBN 1-56238-461-9]. NCCLS, 940 West Valley Road, Suite 1400, Wayne, Pa. 19087-1898 USA.

Thus, it will be appreciated that the present invention provides novel florfenicol-like compounds and methods for their use in the treatment or prevention of bacterial infection in animals or humans.

Although certain embodiments and examples have been used to describe the present invention, it will be apparent to those skilled in the art that changes in the embodiments and examples shown may be made without departing from the scope of this invention.

What is claimed:

1. A compound comprising the chemical formula:

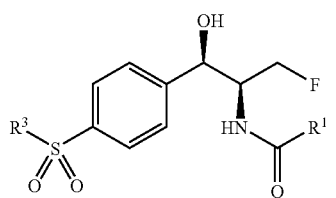

(I)

or a pharmaceutically-acceptable salt thereof or a solvate thereof,
wherein:
R$^1$ is CHCl$_2$, CHClF, CHF$_2$, CHBrCl, CH$_3$, CH$_2$N$_3$, CH$_2$CN, CH(R$^2$)NH$_2$ or CH X$^1$X$^2$;
where R$^2$ is H, CH$_3$ or CH$_2$OH, and
X$^1$ and X$^2$ are independently selected halogens; and
R$^3$ is CH$_2$Cl, CH$_2$F, CHF$_2$, CHCl$_2$ or CH$_2$OH.

2. The compound of claim 1, wherein R$^1$ is CHCl$_2$.

3. The compound of claim 1, wherein R$^3$ is CH$_2$F.

4. The compound of claim 1, wherein X$^1$ and X$^2$ are the same halogen.

5. The compound of claim 1, wherein X$^1$ and X$^2$ are different halogens.

6. The compound of claim 1, wherein the halogen is selected from the group consisting of fluorine, chlorine and bromine.

7. The compound of claim 6, wherein X$^1$ and X$^2$ are both chlorine.

8. A compound of claim 1 selected from the group consisting of

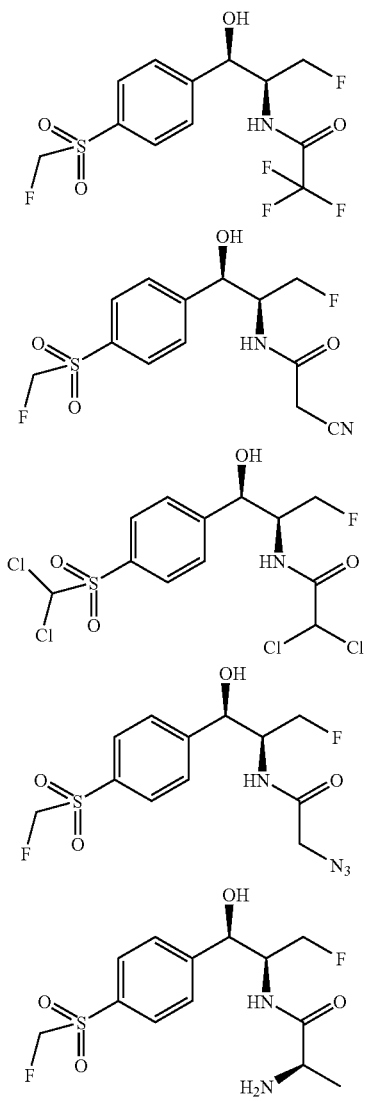

-continued

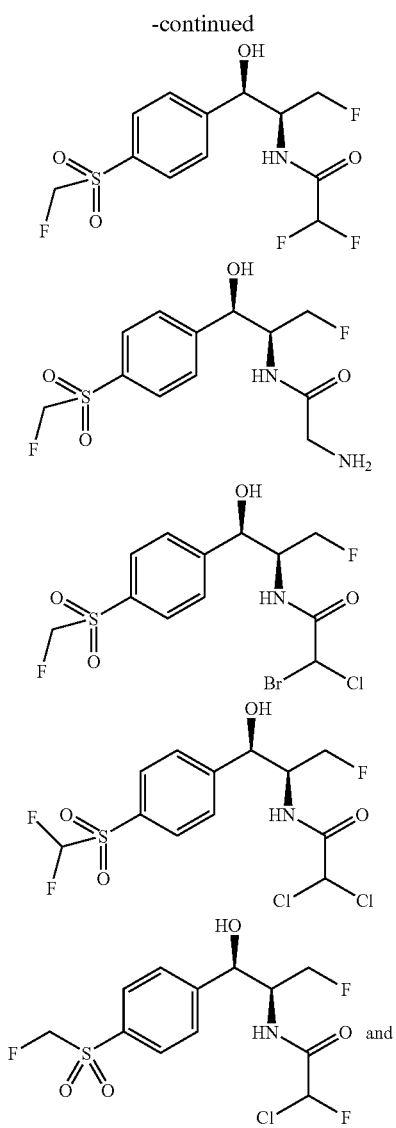

-continued

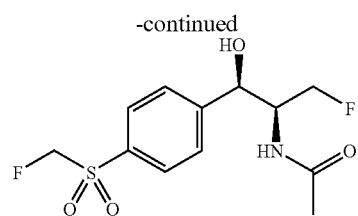

or a pharmaceutically-acceptable salt thereof, or a solvate thereof.

9. A compound of claim 1, having the structure:

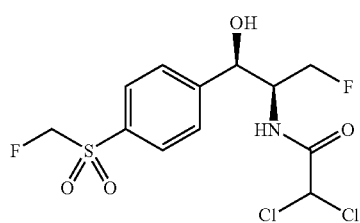

or a pharmaceutically-acceptable salt thereof or a solvate thereof.

10. A compound of claim 1, wherein the compound is substantially enantiomerically pure and has a 1-(R)-2-(S) absolute configuration.

11. A compound of claim 8, wherein the compound is substantially enantiomerically pure and has a 1-(R)-2-(S) absolute configuration.

12. A compound of claim 9, wherein the compound is substantially enantiomerically pure and has a 1-(R)-2-(S) absolute configuration.

13. A pharmaceutical composition comprising a compound of claim 1 and a pharmaceutically-acceptable excipient.

* * * * *

UNITED STATES PATENT AND TRADEMARK OFFICE
CERTIFICATE OF CORRECTION

PATENT NO. : 7,361,689 B2  Page 1 of 1
APPLICATION NO. : 11/018156
DATED : April 22, 2008
INVENTOR(S) : Dale E. Shuster et al.

It is certified that error appears in the above-identified patent and that said Letters Patent is hereby corrected as shown below:

In Claim 8, Column 34, Line 12: replace "pharmaceuticafly-acceptahe" with --pharmaceutically-acceptable--.

Signed and Sealed this

Fifth Day of August, 2008

JON W. DUDAS
*Director of the United States Patent and Trademark Office*